(12) United States Patent
Cheng et al.

(10) Patent No.: US 10,545,140 B2
(45) Date of Patent: Jan. 28, 2020

(54) TEST STRIP HOUSING SYSTEM

(71) Applicants: Kasing Cheng, New York, NY (US); Isaac Lebovits, New York, NY (US)

(72) Inventors: Kasing Cheng, New York, NY (US); Isaac Lebovits, New York, NY (US)

(73) Assignee: Kasaac Laboratories, Corp., New York, NY (US)

( * ) Notice: Subject to any disclaimer, the term of this patent is extended or adjusted under 35 U.S.C. 154(b) by 0 days.

(21) Appl. No.: 14/211,504

(22) Filed: Mar. 14, 2014

(65) Prior Publication Data

US 2014/0271400 A1    Sep. 18, 2014

Related U.S. Application Data

(60) Provisional application No. 61/786,214, filed on Mar. 14, 2013.

(51) Int. Cl.
    *G01N 33/543*    (2006.01)

(52) U.S. Cl.
    CPC ............... *G01N 33/54366* (2013.01)

(58) Field of Classification Search
    CPC ......... G01N 33/54366; G01N 33/4875; G01N 21/75; B01L 3/5023; B01L 2300/0825; B01L 2300/0654; B01L 2300/045; B01L 2200/025; C09B 67/0083
    See application file for complete search history.

(56) References Cited

U.S. PATENT DOCUMENTS

| | | |
|---|---|---|
| 2,739,730 A | 3/1956 | Jonas |
| 4,313,734 A | 2/1982 | Leuvering |
| 4,376,110 A | 3/1983 | David et al. |
| 4,435,504 A | 3/1984 | Zuk et al. |
| 4,703,017 A | 10/1987 | Campbell et al. |
| 4,842,138 A | 6/1989 | Sandel |
| 4,855,240 A | 8/1989 | Rosenstein et al. |
| 4,954,452 A | 9/1990 | Yost et al. |
| 5,028,535 A | 7/1991 | Buechler et al. |
| 5,075,078 A | 12/1991 | Osikowicz et al. |
| 6,150,178 A * | 11/2000 | Cesarczyk ......... A61B 10/0045 422/412 |
| 6,153,147 A * | 11/2000 | Craig ................. B01L 3/5023 422/408 |
| 6,372,516 B1 * | 4/2002 | Sun .................... B01L 3/5023 422/408 |
| 6,808,682 B1 | 10/2004 | Bates et al. |

(Continued)

FOREIGN PATENT DOCUMENTS

WO    2000042430 A1    7/2000

OTHER PUBLICATIONS

Millipore Corporation, "Rapid Lateral Flow Test Strips: Considerations for Product Development", 2002, 42 pages.

(Continued)

*Primary Examiner* — Lore R Jarrett
(74) *Attorney, Agent, or Firm* — Grimes & Yvon LLP

(57) ABSTRACT

The present invention provides an improved diagnostic test strip system comprising one or more of the following safety features: (a) a test strip housing having a sample port of sufficient size to allow placement of a patient's finger or thumb therein, (b) a cover for the test strip housing, and (c) a lock to lock the test strip housing to the cover.

20 Claims, 4 Drawing Sheets

(56) References Cited

U.S. PATENT DOCUMENTS

| | | | |
|---|---|---|---|
| 7,294,502 B2* | 11/2007 | Eckermann | A61B 10/0045 422/537 |
| 2006/0105469 A1* | 5/2006 | Lea et al. | 436/514 |
| 2007/0092401 A1* | 4/2007 | Liao | A61B 10/0038 422/400 |
| 2008/0020482 A1* | 1/2008 | Raj | G01N 33/558 436/165 |
| 2008/0176253 A1* | 7/2008 | Christodoulides et al. | 435/7.21 |
| 2008/0319347 A1* | 12/2008 | Keren | 600/583 |
| 2010/0059533 A1 | 3/2010 | Unger | |
| 2012/0171357 A1 | 7/2012 | Ushiyama | |
| 2012/0329142 A1 | 12/2012 | Battrell | |
| 2014/0187892 A1* | 7/2014 | Gupta | A61B 5/14546 600/367 |

OTHER PUBLICATIONS

International Search Report for PCT application PCT/US2014/027584 entitled Test Strip Housing System filed on Mar. 14, 2014, Applicants Cheng, Kasing, et al.

* cited by examiner

TEST STRIP HOUSING SYSTEM

CROSS-REFERENCE TO RELATED APPLICATIONS

This application claims the benefit of priority of U.S. provisional patent application 61/786,214, filed on Mar. 14, 2013, the contents of which are hereby incorporated by reference in their entirety.

COPYRIGHT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

INCORPORATION BY REFERENCE

For countries and territories that permit incorporation by reference, the text of all documents cited herein is hereby incorporated by reference in its entirety.

BACKGROUND OF THE INVENTION

Test strip devices are widely used in medical diagnostics. Such test strips provide simple portable devices that can be used to detect the presence or absence of a particular analyte of interest in a test sample. Test samples that can be used include urine, serum, blood, saliva, and other biological fluids. The types of analytes that can be detected include infectious agents (such as bacteria and viruses), proteins, non-proteinaceous agents, chemicals, drugs, and the like.

In some typical test strip systems the sample to be tested (i.e. the test sample) is applied to a sample pad located towards one end (the proximal end) of a test strip. After application, the test sample (or components of the test sample) flows laterally through the sample pad and into an adjacent conjugate pad distal to the sample pad. The conjugate pad typically contains conjugates comprising an antibody specific to the analyte of interest conjugated to a labeled/detectable particle. After flowing through the conjugate pad the test sample then flows into an adjacent test membrane distal to the conjugate pad. The test membrane typically has two capture areas—a control capture area and a test capture area. The test capture area typically contains an antibody that is immobilized on the test membrane and that can bind to the analyte of interest. As the test sample flows through the test membrane from the proximal end to the distal end, complexes containing the analyte of interest bound to a labeled conjugate will accumulate at the test line. The control capture area typically contains an antibody that is immobilized on the test membrane and that can bind to the labeled conjugates. As the test sample flows through the test membrane labeled conjugate molecules will accumulate at the control line. The accumulation of these complexes and/or conjugates at the test and control areas can be visualized as a result of the detectable label in the conjugate molecules, which may result in, for example, the appearance of a colored line.

There are a wide variety of different test strip systems that can be used for a wide variety of different diagnostic applications. For example, some test strip systems use a direct con-competitive antibody reaction scheme, while others use an indirect competitive antibody reaction scheme. Similarly, different test strip systems can be used for different types of test samples (such as blood, serum, urine, and the like) and for detection of different types of analytes (such as proteins, infectious agents, drugs of abuse, and the like). Regardless of the details of the test strip system, in practice, diagnostic test strips are frequently provided inside a housing (also referred to as a cassette or cartridge) that is made of plastic or some other suitable material. Such test strip housings typically have at least two types of openings. The first type of opening is a sample port—through which the test sample can be applied to the sample pad portion of the test strip using a pipette or similar device. The second type of opening is a result viewing port—through which the test and/or control areas of the test membrane can be viewed.

Prior to the present invention test strip housings were typically provided with a small sample port configured to allow application of a test sample to the sample pad area of a test strip using a pipette or some other similar device. Using these prior systems a test administrator would typically have to obtain a test sample, such as blood, from a patient and then transfer that test sample to the sample port of a test strip housing a pipette, a dropper, a syringe, a needle, or the like. The need to handle and transfer the test sample in this way increased the risk that test administrators or others could come into contact with a spilled or inaccurately placed patient sample or with a contaminated pipette. In addition, prior to the present invention test strip housings were typically provided with sample ports and result viewing ports that were open/uncovered such that it could be possible for a test administrator or other person to come into contact with a contaminated test strip. Furthermore, these prior test strip systems resulted in the generation of additional hazardous waste in the way of used/contaminated pipettes that required special disposal systems and careful handling.

BRIEF SUMMARY OF THE INVENTION

The present invention provides an improved test strip housing system that can be used in conjunction with any diagnostic test strips. The improved test strip housing system of the present invention is particularly advantageous for use with biological test samples that may contain an infectious agent or that may otherwise be hazardous and/or pose some risk to a test administrator or others.

As mentioned above, prior art test strip housings typically had a sample port that was small in size such that a pipette (or similar device) was required to transfer a test sample through the sample port and onto the test strip. It is an object of the invention to eliminate the need to use a pipette (or similar device) in this way by providing a test strip housing having a sample port or sample port insert that is of sufficient size and shape that a patient's finger or thumb can be placed directly into the sample port or sample port insert and thereby allow direct transfer of a test sample (typically blood) from a patient's finger or thumb to the sample pad portion of a test strip. Thus, when using a test strip housing according to the present invention a patient or a test administrator can draw blood from a patient's finger or thumb (for example using a lancet or the like), and then the patient can place that finger or thumb into the sample port or sample port insert allowing transfer of a blood sample directly from the patient's finger or thumb to the sample pad portion of a test strip. It is also an object of the present invention to provide a test system that has additional features aimed at minimizing the risk that a person handling a test strip could come into contact with a potentially hazardous patient test sample through contact with a contaminated test strip or test strip housing. The test strip system of the present invention utilizes a combination of one or more of the following safety enhancing features to minimize these risks: (a) a test strip housing having large sample port, (b) a cover for the test strip housing, and (c) a lock to lock the test strip housing to the cover.

In one embodiment the present invention provides a diagnostic test strip system comprising a test strip housing, wherein the test strip housing comprises a sample port of sufficient size to allow placement of a human patient's finger or thumb therein, and a result viewing port. In one embodiment the sample port comprises a sample port insert.

In some embodiments the diagnostic test strip system further comprises a cover. In some embodiments the cover is transparent or comprises a transparent window. In some embodiments the cover is slideably positioned on the test strip housing such that the cover can be moved from a "first position" to a "second position" on the test strip housing. When the cover is in its first position on the housing it does not cover the sample port, leaving it open and available for placement of a test sample, but when the cover is in its second position on the test strip housing it covers the sample port preventing application of a test sample and also preventing a person handling the test strip housing from coming into contact with the sample port, the sample port insert, the test strip below the sample port, or the area of the housing surrounding the sample port. In some preferred embodiments when the cover is located at its second position on the test strip housing it also covers the result viewing port, thereby preventing a person handling the test strip housing from coming into contact with the result viewing port, the test strip below the result viewing port, or the area of the housing around the result viewing port. In embodiments where the cover covers the result viewing port it is preferable that the cover be transparent, or have a transparent window, such that the result viewing port remains visible even when the cover is in its second position on the test strip housing.

In some embodiments the test strip housing system of the invention also comprises a locking system to lock the cover to the housing when it is located at the second position on the test strip housing. In some such embodiments the locking system comprises a protrusion located on either the housing or the cover, and a receptacle located on either the housing or the cover. The receptacle and the protrusion are positioned such that when the cover is located at its second position on the test strip housing the protrusion engages with the receptacle thereby locking the cover to the test strip housing.

These and other features of the invention are described in more detail in the description below, as well as in the drawings and claims that form part of this patent application.

BRIEF DESCRIPTION OF THE DRAWINGS

FIG. 8 is a perspective view of an exemplary test strip housing, cover, and lock.

DETAILED DESCRIPTION OF THE INVENTION

Figure 1:
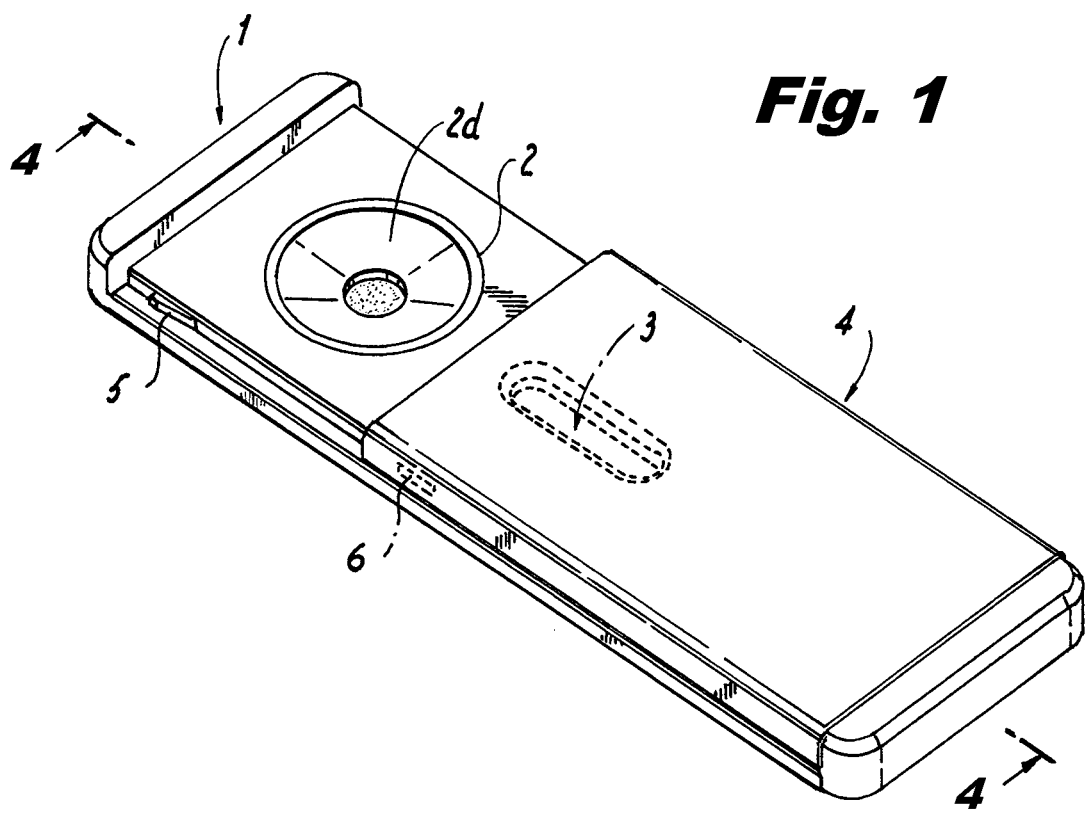
FIG. 1 is a perspective view of an exemplary test strip housing shown with a circular sample port and a cover on the test strip housing in a first position.

As used herein the terms "about" and "approximately" when used in conjunction with a quantitative value are intended to mean plus or minus 20% of the quantitative value described.

As used herein the terms "rectangle" and "rectangular" are used to refer to a classic rectangle and also to shapes that are generally rectangular in form but may have some modifications, such as having one or more rounded or angled corners, or having alternating sides that are not precisely parallel or are not precisely of equal length.

As used herein the term "square" is used to refer to a classic square and also to shapes that are generally square in form but may have some modifications, such as having one or more rounded or angled corners, or having sides that are not precisely of equal length.

As used herein the terms "circle" and "circular" are used to refer to classic/perfect circles and also to shapes that are generally, but not precisely, circular in form.

As used herein the term "oval" is used to refer to classic oval or elliptical shapes and also to shapes that are generally, but not precisely, oval or elliptical in form.

As used herein the terms "polygon" and "polygonal" are used to refer to any polygonal or generally polygonal shape, including convex polygonal shapes, regular and irregular polygonal shapes, and polygonal shapes having either and odd or even number of sides, including, but not limited to polygons having a square, rectangular, pentagonal, hexagonal, hepatagonal, octagonal, nonagonal, decagonal or dodecagonal shape. In some embodiments the polygonal shapes are convex polygons having an even number of sides, such as hexagons, octagons, decagons, and the like. The terms "polygon" and "polygonal" as used herein also refer shapes that are generally polygonal in form but may have some modifications, such as having one or more rounded corners or sides.

As described above the present invention provides an improved test strip housing system that utilizes a combination of one or more of the following safety enhancing features: (a) a test strip housing having a sample port of sufficient size to allow placement of a patient's finger or thumb therein, (b) a cover for the test strip housing, and (c) a lock to lock the test strip housing to the cover. FIGS. 1 to 8 show some exemplary test strip housings and covers according to the invention. While the designs shown in the Figures are illustrative of the various different safety features of the test strip system of the present invention, the invention is not limited to the specific designs provided in the drawings. Rather variations and modifications of the specific designs shown in the Figures are contemplated and are within the scope of the present invention, as described throughout and as would be understood by those of ordinary skill in the in the art.

FIG. 1 is a perspective view of an exemplary test strip housing 1 with an exemplary sliding cover 4. Opening 2 is a sample port comprising a sample port insert 2d and is located towards the proximal end of the housing, i.e. the end at which the sample pad portion of an internal test strip would be located. Opening 3 is a result viewing window and is located distal to the sample port. Although only one sample port 2 and one result viewing window 3 are shown, multiple sample ports or result viewing windows may be present. The sample port 2 forms an opening in the material from which the test strip housing 1 is made and allows a test sample to be applied through the sample port insert 2d to the sample pad area of a test strip located inside the test strip housing 1. In FIG. 1 the sample port 2 and sample port insert 2d are shown as having a circular shape and the result viewing window 3 is shown as having an oval shape. However, the sample port, sample port insert and result viewing window may be any suitable rounded or polygonal shape, such as square, circular, oval, and the like. FIG. 1 shows a cover 4 positioned over the distal portion of a test strip housing 1. In the embodiment shown the cover 4 slides along the top surface of the test strip housing and is made of a transparent material such that the top surface of the underlying test strip housing 1 is visible through the cover 4. The cover 4 is shown in a first position in which it covers the result viewing window 3 but does not cover the sample port 2 and sample port insert 2d. A test sample may be applied to the sample port insert 2d while the cover 4 is in this first position. FIG. 1 also shows an exemplary locking system used to secure a cover 4 to a test strip housing 1. In use, a test sample can be applied to the sample port insert 2d while the cover 4 is in the first position, shown in FIG. 1, and then the cover 4 may be moved to and locked at its second position (shown in FIG. 2). In the embodiment shown in FIG. 1, the locking system comprises a protrusion 5 located at the end of the test strip housing 1, and a receptacle 6 located at the end of the cover 4. After application of the test sample to the sample port insert 2d the cover 4 is slid from its first position (FIG. 1) to its second position (FIG. 2) and secured at this second position by insertion of the protrusion 5 into the receptacle 6.

Figure 2:
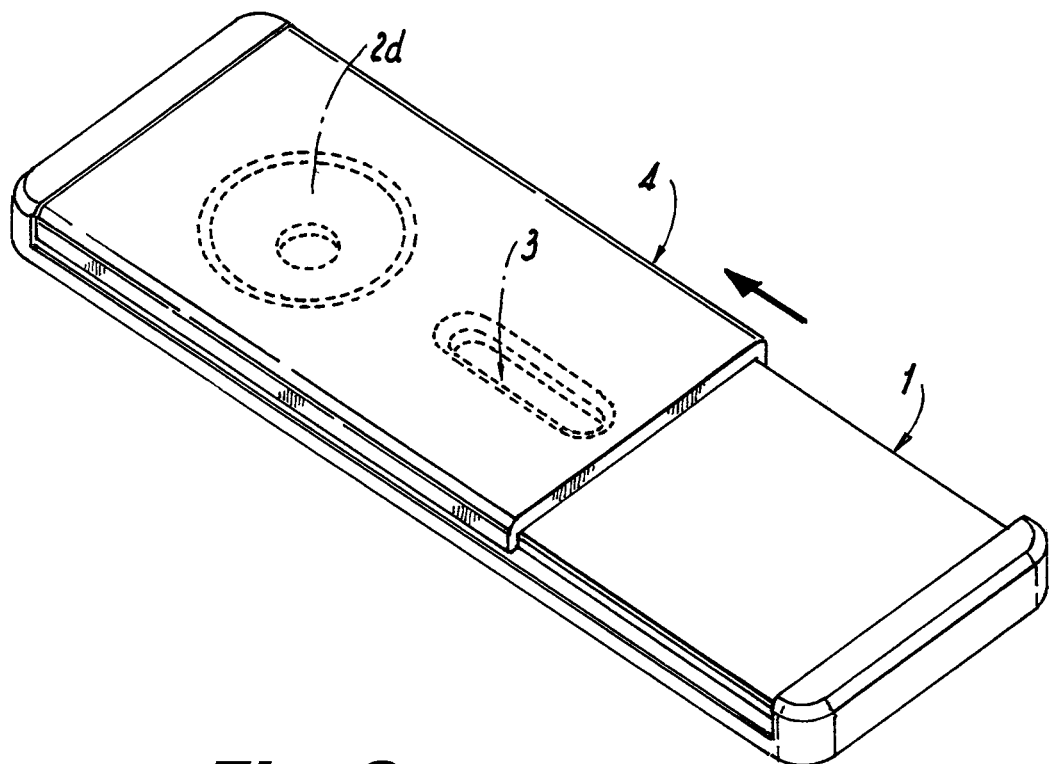
FIG. 2 is a perspective view of an exemplary test strip housing shown with a circular sample port and a cover on the test strip housing in a second position.

FIG. 2 shows a cover 4 positioned over a test strip housing 1 at a second position in which it covers the proximal portion of the test strip housing—here covering both the result viewing window 3 and the sample port 2 and sample port insert 2d. In the embodiment shown the cover 4 is made of a transparent material such the underlying test strip housing 1 is visible through the cover 4. The arrow in FIG. 2 represents the direction of movement when the cover 4 is moved from its first position to its second position.

Figure 3:
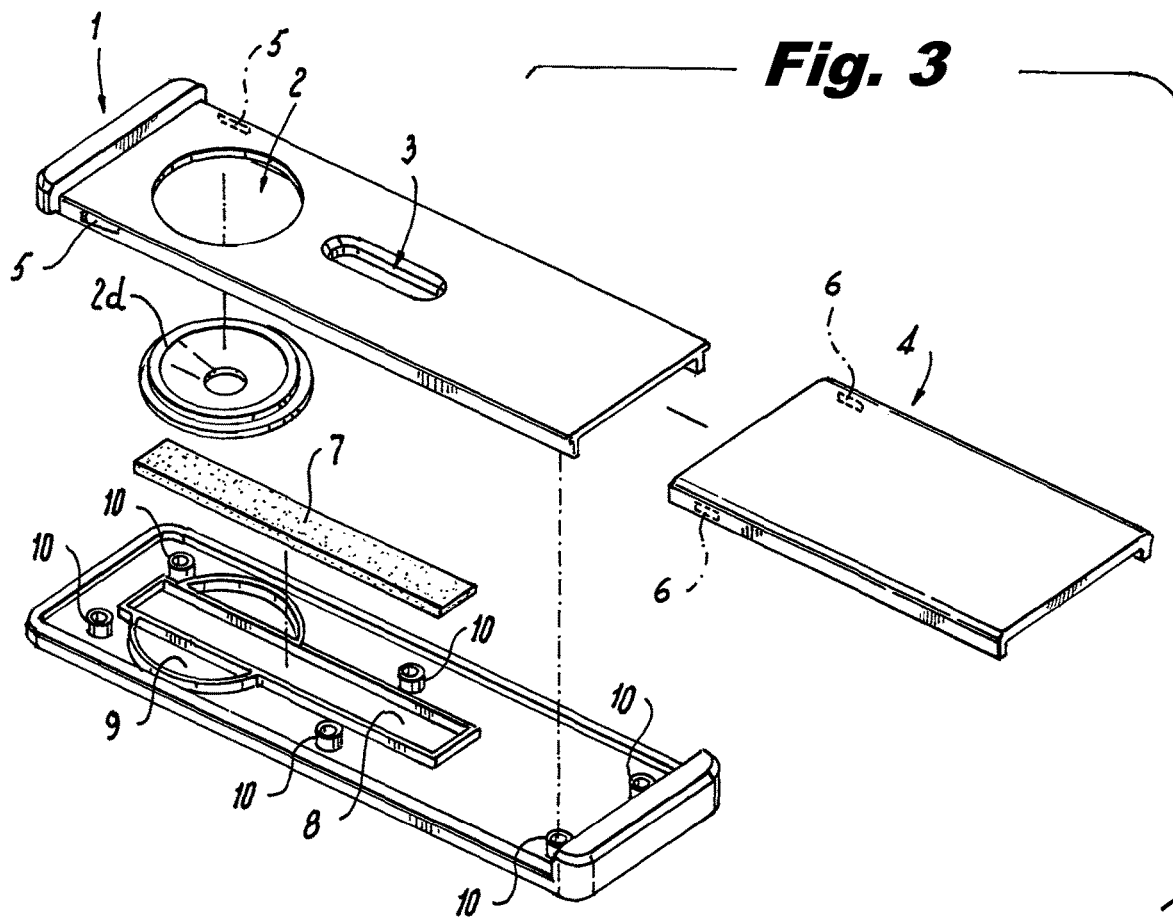
FIG. 3 is an exploded view of an exemplary test strip housing, cover, sample port insert and test strip.

FIG. 3 is an exploded view of an exemplary test strip housing 1, an exemplary cover 4, an exemplary circular sample port 2 comprising a circular sample port insert 2d, an exemplary oval result viewing window 3, an exemplary test strip 7 and various internal features of the test strip housing, including a test strip indent 8, a sample port insert indent 9 and structures 10 for facilitating assembly of the test strip housing. FIG. 3 also shows an exemplary locking system with protrusions 5 and receptacles 6 used to secure a cover 4 to a test strip housing 1.

Figure 4:
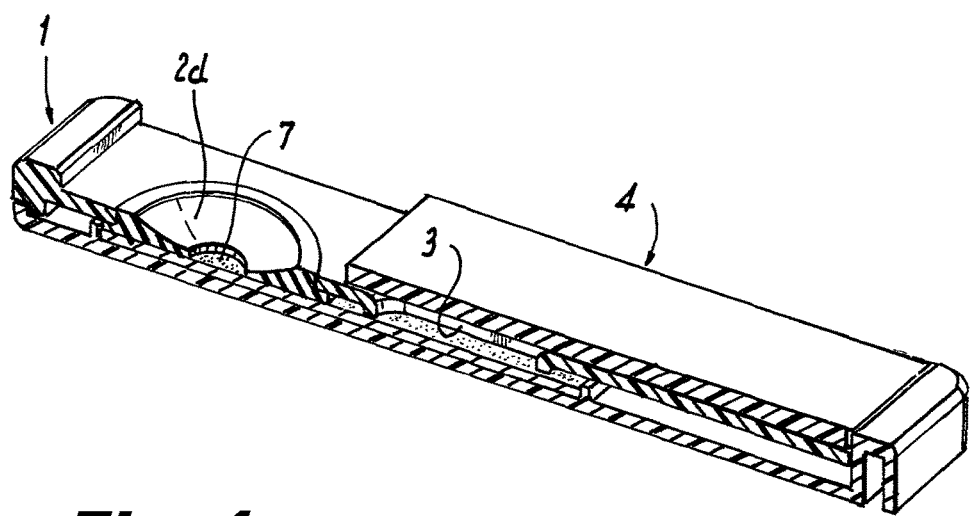
FIG. 4 is a cross-section view of an exemplary test strip housing, cover, sample port insert and test strip (as shown in the perspective view in FIG. 1).

FIG. 4 is a cross-section view of the exemplary test strip housing shown in FIG. 1. FIG. 4 shows exemplary internal and external components and structures of the test strip housing 1, including a cover 4, a sample port insert 2d, a result viewing window 3, and a test strip 7.

Figure 5:
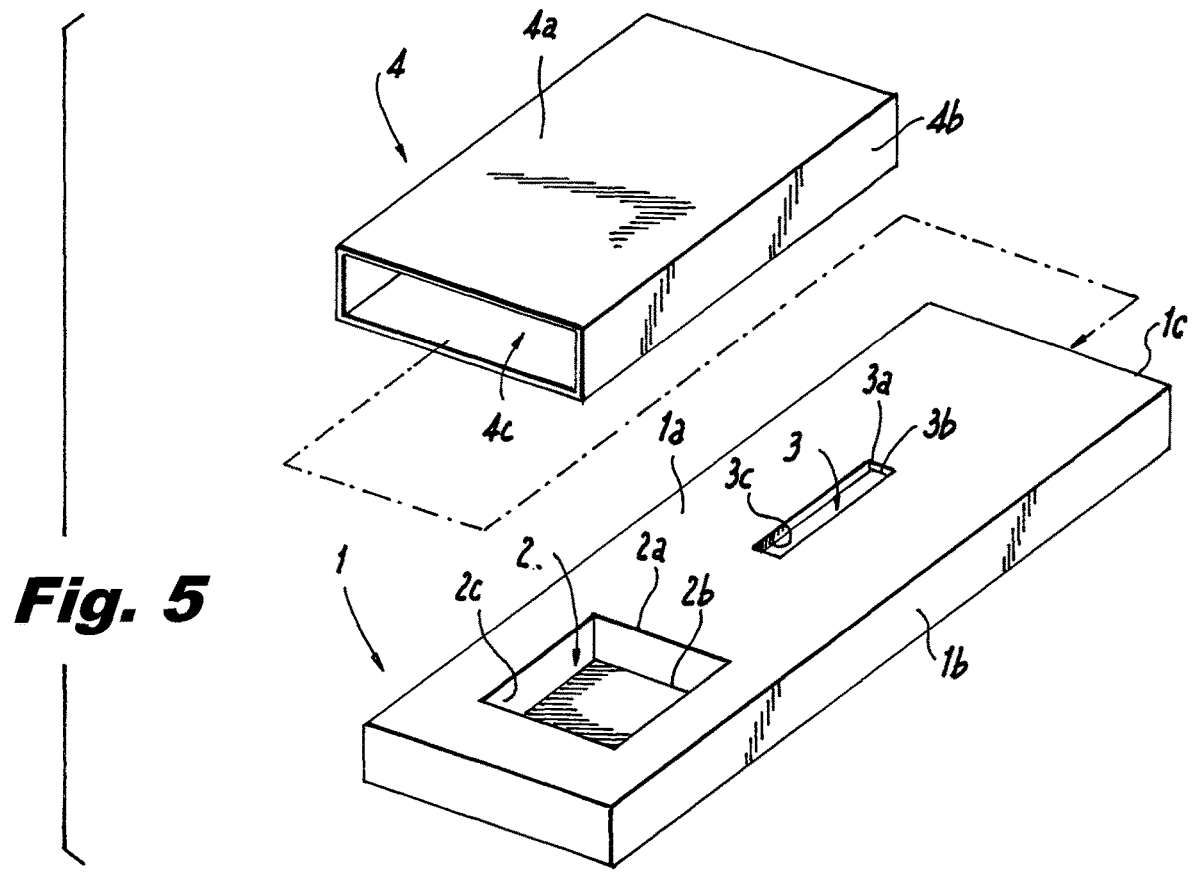
FIG. 5 is a perspective view of an exemplary test strip housing (bottom) and a cover for the test strip housing (top).

FIG. 5 is a perspective view of an exemplary test strip housing 1 and an exemplary cover 4—which are shown separately. In this perspective view the top surface 1a, one side surface 1b, and one end surface 1c (the distal end surface) of the test strip housing 1 can be seen. Two openings are shown in the top surface 1a of the housing. Opening 2 is a sample port and is located towards the proximal end of the housing, i.e. the end at which the sample pad portion of an internal test strip would be located. Opening 3 is a result viewing window and is located distal to the sample port. Although only one sample port 2 and one result viewing window 3 are shown, multiple sample ports or result viewing windows may be present. The sample port 2 forms an opening in the material from which the test strip housing 1 is made and allows a test sample to be applied to the sample pad area of a test strip located inside the test strip housing 1. In FIG. 5 the sample port 2 is shown as having a rectangular shape. However, the sample port may be any suitable rounded or polygonal shape, such as square, circular, oval, and the like. The sample port has a top edge 2a on the top surface 1a of the test strip housing, a bottom edge 2b that is below the top surface 1a of the test strip housing but above the test strip itself, and sidewalls 2c. The side walls 2c may be straight, beveled, chamfered, or any other suitable shape. The result viewing window 3 forms another opening in the material from which the test strip housing 1 is made and allows a result area of a test strip located within the test strip housing to be viewed. In FIG. 5 the result viewing window 3 is shown as having a rectangular shape. However, the result viewing window may be any suitable shape rounded or polygonal shape, such as square, circular, oval, and the like. The result viewing window has a top edge 3a on the top surface 1a of the test strip housing, a bottom edge 3b that is below the top surface of the top surface 1a of the test strip housing but above the result area of the test strip itself, and sidewalls 3c. The side walls may be straight, beveled, chamfered, or any other suitable shape. Although not shown in this Figure, in use a test strip would typically be contained inside the test strip housing 1 (as shown in FIGS. 3 and 4). FIG. 5 also shows a cover 4 for use with the test strip housing 1. In this perspective view the top surface 4a, one side surface 4b, and one open end 4c of the cover 4 can be seen.

Figure 6:
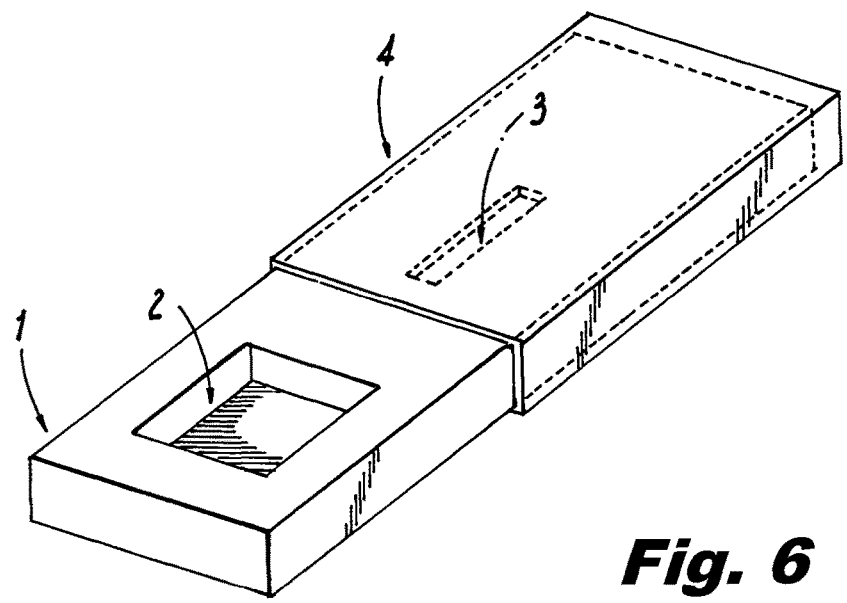
FIG. 6 is a perspective view of an exemplary test strip housing shown with a cover on the test strip housing in a first position.

FIG. 6 shows a cover 4 positioned over the distal portion of a test strip housing 1. In the embodiment shown the cover 4 is made of a transparent material such the underlying test strip housing 1 is visible through the cover 4. The cover 4 is shown in a first position in which it covers the result viewing window 3 but does not cover the sample port 2. A test sample may be applied to the sample port 2 while the cover 4 is in this first position.

Figure 7:
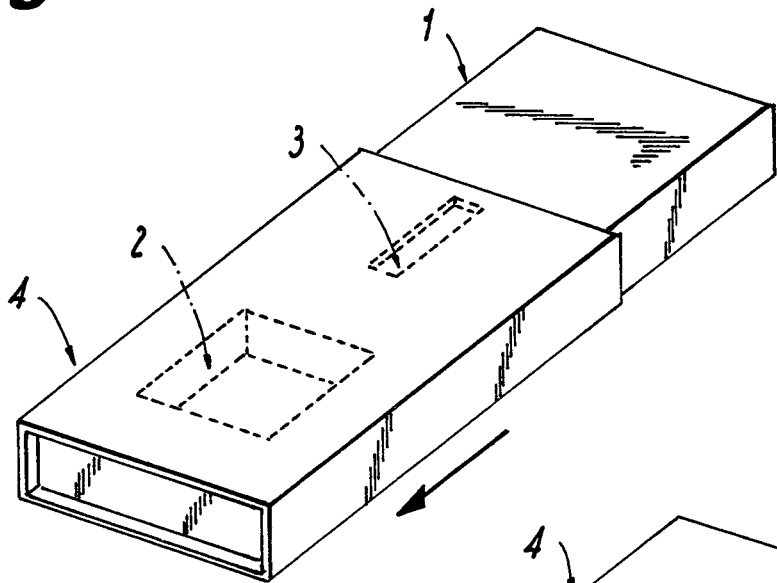
FIG. 7 is a perspective view of an exemplary test strip housing shown with a cover on the test strip housing in a second position.

FIG. 7 shows a cover 4 positioned over a test strip housing 1 at a second position in which it covers the proximal portion of the test strip housing—here covering both the result viewing window 3 and the sample port 2. In the embodiment shown the cover 4 is made of a transparent material such the underlying test strip housing 1 is visible through the cover 4.

In use, a test sample may be applied to the sample port 2 while the cover 4 is in its first position (shown in FIG. 6) and then the cover 4 may be moved to its second position (shown in FIG. 7). The arrow in FIG. 7 represents the direction of movement when the cover 4 is moved from its first position to its second position.

Figure 8A:
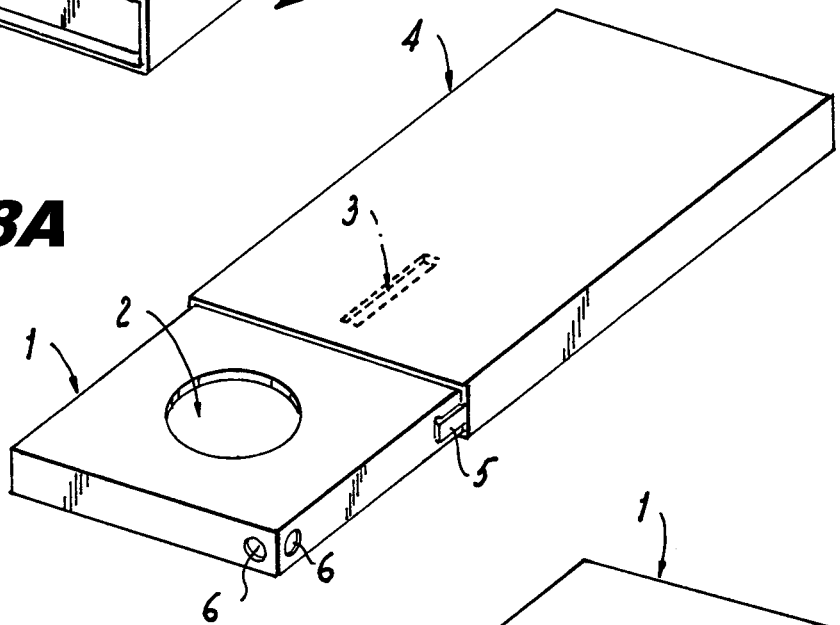
FIG. 8A illustrates the cover placed onto the test strip in a first position.
Figure 8B:
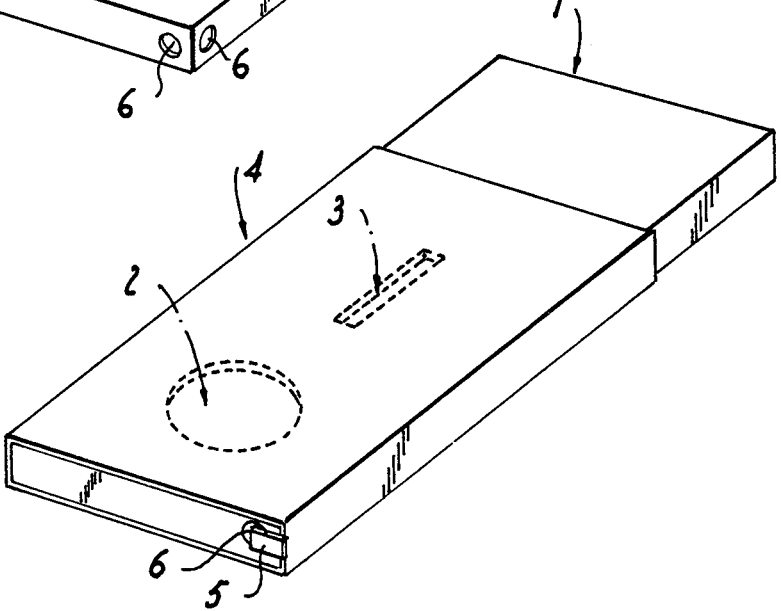
FIG. 8B illustrates the cover placed onto the test strip in a second position.

FIG. 8 shows an exemplary locking system used to secure a cover 4 to a test strip housing 1. In use, a test sample can be applied to the sample port 2 while the cover 4 is in the first position (shown in FIG. 8A), and then the cover 4 may be moved to and locked at its second position (shown in FIG. 8B). In the embodiment shown in FIG. 8 the locking system comprises a protrusion 5 (here, a hook) located at the end of the cover 4, and a receptacle 6 (here, a hole) located at the end of the test strip housing 1. After application of the test sample to the sample port 2 the cover 4 is slid from its first position (FIG. 48A) to its second position (FIG. 8B) and secured to the test strip housing 1 at this second position by insertion of the protrusion 5 into the receptacle 6.

While the designs shown in the Figures are illustrative of the various different safety features of the test strip system of the present invention, the invention is not limited to the specific designs provided in the drawings. Some of the design variations and modifications that are within the scope of the invention are described in further detail below and elsewhere in the specification and claims.

Test Strip Housing

The test strip housing according to the present invention can be made of any suitable material including, but not limited to, plastic, such as a biocompatible plastic. The housing may be made of a material that is opaque, translucent, or transparent. In FIGS. 1-8 the test strip housing 1 is shown as having a rectangular box-like shape. However, variations in both the shape and size of the housing are also within the scope of the invention, and any suitably shaped and sized test strip housing can be used. For example, in some embodiments the housing can have rounded ends and/or rounded sides and/or the body of the housing can have a more cylindrical shape. In some embodiments the housing can have one or more openings in addition to the sample port and result viewing ports described herein. For example, the housing can have one or more openings located over a conjugate pad area and/or over an absorbent pad or wicking area of an internal test strip or other openings designed to facilitate manufacture or assembly of the housing. In some embodiments the housing can have labeling on its surface, for example to identify the type of test strip located within the housing, the location of the sample port, the location of the test and/or control areas in the result viewing port, and the like. Test strip housings according to the present invention may have various internal structural features as needed. For example, the test strip housings may have internal grooves, indentations, holes, walls, bars, or pins to hold a test strip in place inside the housing and to maintain the test strip in the correct position with respect to the openings in the housing—for example to keep the sample pad area and test strip in alignment with the sample port in the housing and to keep the test and control result areas of the test membrane in alignment with the result viewing port. The test strip housing may also have internal structural features that facilitate assembly of the test strip housing, for example to secure or attach the top portion of the test strip housing to the bottom portion of the test strip housing. In FIG. 3, several exemplary internal structural features are illustrated, including a test strip indent 8, sample port insert indent 9, and structures 10 to facilitate alignment and assembly of the test strip housing.

The exemplary housings shown in FIGS. 1 to 8 may be held in a hand, laid flat on a table or other surface, or tilted or propped up against a surface while in use—for example to facilitate placement of a test sample and/or viewing of the results. Although not illustrated in the drawings, in some embodiments the housing may also comprise, or be used in conjunction with, a stand to facilitate positioning and angling of the test strip housing as desired. Thus, in some embodiments the housing may comprise a stand element, for example similar to a picture frame stand.

Sample Port

As used herein the term "sample port" refers to an opening in a test strip housing through which a test sample can be applied. In one embodiment, the present invention provides a test strip housing having one or more sample ports that are of a sufficient size and shape to allow direct transfer of a test sample (such as blood) from a patient's finger or thumb through the sample port and onto the sample pad portion of a test strip positioned inside the housing and below the sample port. In the Figures provided here exemplary test strip housings having a single sample port are shown. However, test strip housings according to the invention may have one, two, three, four, or more sample ports, as desired.

As described above, prior art test strip housings typically had a sample port that was small in size such that a pipette (or similar device) was required to transfer a test sample through the sample port and onto the test strip. It is an object of the invention to eliminate the need to use a pipette (or similar device) in this way by providing a test strip housing having a sample port or sample port insert that is of sufficient size and shape that a patient's finger or thumb can be placed directly into the sample port or sample port insert and thereby allow direct transfer of a test sample (typically blood) from a patient's finger or thumb to the sample pad portion of a test strip. Thus, when using a test strip housing according to the present invention a patient or a test administrator can draw blood from a patient's finger or thumb (for example using a lancet or the like), and then the patient can place that finger or thumb into the sample port or sample port insert allowing transfer of a blood sample directly from the patient's finger or thumb to the sample pad portion of a test strip.

A sample can be applied to the test strip through the sample port of the test strip housing or through a sample port insert situated partly or entirely within the sample port. The sample port or the sample port insert can be of any desired shape or size to facilitate placement of a sample onto the sample pad portion of a test strip. In FIGS. 1, 3 and 4, an exemplary sample port insert is illustrated as element 2*d*, however, all of the exemplary sizes and shapes described herein for a sample port will apply equally to a sample port insert. In some embodiments, the sample port insert can have the same size or shape as the sample port, or the sample port insert can have a different size or shape. In other embodiments, the sample port insert and sample port may have the same shape and different sizes; or the sample port insert and sample port may be the same size but have different shapes. If a sample port insert will be inserted into a sample port, then the sample port will ideally have a size and shape such that the sample port insert will fit into the sample port. All of the exemplary sizes and shapes described herein for a sample port will apply equally to a sample port insert.

According to one embodiment of the invention, the sample port insert has a size and shape sufficient to allow placement of a patient's finger or thumb into the port such that a sample of blood on the patient's finger or thumb can be applied directly (i.e. without the need to use a pipette or similar device) to the sample pad portion of a test strip located inside the housing. Suitable shapes for the sample port insert include, but are not limited to, circular, oval, square, rectangular, and the like. The sample port insert will typically have a top edge(s) at or near the top surface of the housing, a bottom edge(s) below the top surface of the housing and above or contacting the test strip itself (see, for example, element 2d in FIG. 4), and walls. The top and bottom of the sample port insert may comprise straight edges, curved edges, or a combination of straight and curved edges, and comprise openings of any suitable shape. For example, in one embodiment an opening may be circular or oval shaped. In another embodiment an opening may have any suitable polygonal shape, including, but not limited to, a triangular, square, rectangular, pentagonal, or hexagonal shape. The walls of the sample port insert may run perpendicular to the top surface of the test strip housing or not, and may be straight, curved, beveled, chamfered, or any other suitable shape, as desired. The top and bottom of the sample port insert may be comprise straight edges, curved edges, or a combination of straight and curved edges, and may form an opening of any suitable shape. For example, in one embodiment the sample port insert may be circular or oval shaped. In another embodiment the sample port insert may have any suitable polygonal shape, including, but not limited to, a triangular, square, rectangular, pentagonal, or hexagonal shape. The sample port insert may be straight, curved, beveled, chamfered, or any other suitable shape, as desired. The top and bottom edges of the sample port insert may have the same size and/or shape as each other or may have different sizes and/or shapes. The sample port inserts shown in FIGS. 1, 3 and 4, which are exemplary only, have top and bottom edges that have the same circular shape but differ in size, with the bottom edge having smaller dimensions than the top edge, resulting in a tapered shape. However, sample port inserts can have top and bottom edges that have the same size or different shape as desired. The surface of the sample port insert could be of any suitable form, including, but not limited to, being curved, straight, beveled, or chamfered. In other embodiments, the sample port insert may have a bottom edge that has different geometric shape as compared to the top edge, for example being square or rectangular at the top edge and circular or oval shaped at the bottom edge.

The bottom edge of the sample port insert will typically extend below the top surface of the test strip housing and the bottom edge of the insert will typically touch or fit against the test strip inside the test strip housing, such that the opening in the bottom edge of the insert is aligned above the test strip to allow application of a test sample though the opening onto the sample pad portion of the test strip. In some embodiments, the top edge of the sample port insert can be flush or level with the area of the housing around the top edge of the sample port opening. In other embodiments, the top edge of the sample port insert may have dimensions larger than the opening of the sample port, such that when the sample port insert is in the sample port, the top edge of the sample port insert contacts or overlays the exterior of the top surface of the test strip housing (for example, if the top edge of the insert is slightly higher than the top edge of the sample port opening) or contacts or extends along the interior of the top surface of the test strip housing. In some embodiments, the bottom edge of the sample port insert may contact or extend along the interior of the top surface of the test strip housing (see, for example element 2d in FIG. 4) For example, in FIGS. 1 and 4, the sample port insert (element 2d) has a top edge that is flush with test strip housing and a bottom edge that extends along the interior of the top surface of the test strip housing.

The sample port insert may contact the sidewalls of the sample port, or it may not. For example the sample port insert may be narrower than the sample port at one or more points, such as if the sample port has straight sidewalls that run perpendicular to the top edge of the sample port, and the walls of the inserted sample port insert are tapered. The bottom edge of the sample port insert may contact the bottom edge of the sample port, or it may not. For example, the sidewalls of the sample port may not be of sufficient height to contact the test strip so that the bottom edge of the sample port is above the test strip and does not contact the test strip, and the sample port insert is of sufficient height such that the bottom edge of the sample port insert contacts the test strip. Typically, the top edge of the sample port insert will contact the top edge of the sample port. In some embodiments, the sample port insert can be positioned and aligned by indents, grooves, walls or other similar internal structures on the interior of the test strip housing.

A sample port insert can be made of any suitable material including, but not limited to, plastic or rubber. A sample port insert can also comprise a coating or finish, for example, to facilitate flow of the sample through the sample port and onto the test strip. To prevent spillage or leakage of sample into the interior of the test strip housing, the sample port insert will ideally fit tightly against the test strip housing and against the test strip, however, in some embodiments, gaskets or seals or the like can be used to further secure the sample port insert in the test strip housing.

The sample port insert may be used to customize the size and shape of a sample port. For example, a test strip housing may be manufactured with a standard or generic sample port size and shape, and various sample port inserts may be used to achieve the desired size and shape of the sample port.

While the test strip housings of the invention are designed to facilitate placement of a patient's finger or thumb into the sample port or sample port insert, a user can employ other means (such as using a pipette) to apply a test sample to a test strip if desired, for example if a test sample other than blood (such as urine, saliva, serum, and the like) is to be used or if placement of a patient's finger into the sample port is not practicable. However, a key feature of the test strip housings of the invention is that, if desired, a patient's blood sample can be transferred directly from a patient's finger to the test strip with ease—without, for example, the need to carefully align a blood drop on a patient's finger over a small sample port, and without significant risk of a blood sample being misplaced or smeared over the area of the housing around the sample port during the process.

Typically from about 15 microliters to about 30 microliters of a sample, such as a blood sample, will be applied to the test strip via the sample port or the sample port insert. In some embodiments the amount of the sample, such as a blood sample, applied to the test strip will be measured. Accordingly, in some embodiments the test strip housing system of the present invention also includes a means for measuring the amount of a sample that is applied to the test strip or through the sample port or the sample port insert. For example, one or more sidewalls of the sample port (see, for example element 2c of the Figures) or the sample port insert (see, for example, element 2d of the Figures) may comprise labels or markings for measuring the amount of a sample that is applied to the test strip or through the sample port or sample port insert.

According to one embodiment of the invention, the sample port can be any opening in the test strip housing that has a size and shape sufficient to allow placement of a patient's finger or thumb into the port such that a sample of blood on the patient's finger or thumb can be applied directly (i.e. without the need to use a pipette or similar device) to the sample pad portion of a test strip located inside the housing. Suitable shapes for the sample port include, but are not limited to, circular, oval, square, rectangular, and the like. The opening in the housing that constitutes the sample port will typically have a top edge(s) on the top surface of the housing (see, for example, element 2a in the Figures), a bottom edge(s) below the top surface of the housing and above the test strip itself (see, for example, element 2b in the Figures), and sidewalls (see, for example, element 2c in the Figures). The top and bottom of the sample port opening may be comprise straight edges, curved edges, or a combination of straight and curved edges, and may form an opening of any suitable shape. For example, in one embodiment the opening may be circular or oval shaped. In another embodiment the opening may have any suitable polygonal shape, including, but not limited to, a triangular, square, rectangular, pentagonal, or hexagonal shape. The side walls of the opening that constitutes the sample port may run perpendicular to the top surface of the test strip housing or not, and may be straight, curved, beveled, chamfered, or any other suitable shape, as desired. The top and bottom edges of the sample port opening may have the same size and/or shape as each other or may have different sizes and/or shapes. The sample ports shown in FIGS. 5 to 7, which are exemplary only, have top and bottom edges that are both of the same size and rectangular shape as each other. However, sample ports can have top and bottom edges that differ in size or shape as desired. For example, in some embodiments, the sample port may have a bottom edge that has smaller dimensions than the top edge resulting in a tapered opening. The sides of such a tapered opening could be of any suitable form, including, but not limited to, being curved, straight, beveled, or chamfered. In other embodiments, the sample port may have a bottom edge that has different geometric shape as compared to the top edge, for example being square or rectangular at the top edge and circular or oval shaped at the bottom edge. In some embodiments, the desired size and shape of the sample port may be achieved by a sample port insert (see, for example element 2d in FIGS. 1 to 4).

The sample port or sample port insert can be of any size that is sufficient to allow placement of a patient's finger or thumb into the port such that a sample of blood on the patient's finger or thumb can be applied directly to the sample pad portion of a test strip located inside the housing.

The sample port shapes and sizes described in this paragraph can apply equally to the sample port and the sample port insert. For example, in several embodiments the present invention provides a test strip housing having a circular sample port that is from 6-to 20 millimeters in diameter. In one embodiment the circular sample port is from 6-to 15 millimeters in diameter. In another embodiment the circular sample port is from 6-to 10 millimeters in diameter. In another embodiment the circular sample port is from 7-to 20 millimeters in diameter. In another embodiment the circular sample port has an opening that is from 7-to 15 millimeters in diameter. In another embodiment the circular sample port has an opening that is from 7-to 10 millimeters in diameter. In another embodiment the circular sample port is from 8-to 20 millimeters in diameter. In another embodiment the circular sample port is from 8-to 15 millimeters in diameter. In another embodiment the circular sample port is from 8-to 10 millimeters in diameter. In another embodiment the circular sample port is from 9-to 20 millimeters in diameter. In another embodiment the circular sample port is from 9-to 15 millimeters in diameter. In another embodiment the circular sample port is from 9-to 10 millimeters in diameter. In another embodiment the circular sample port is from 10-to 20 millimeters in diameter. In another embodiment the circular sample port is from 10-to 15 millimeters in diameter. In another embodiment the circular sample port is 6 millimeters in diameter. In another embodiment the circular sample port is approximately 6 millimeters in diameter. In another embodiment the circular sample port is at least 6 millimeters in diameter. In one embodiment the circular sample port is 7 millimeters in diameter. In another embodiment the circular sample port is approximately 7 millimeters in diameter. In another embodiment the circular sample port is at least 7 millimeters in diameter. In one embodiment the circular sample port is 8 millimeters in diameter. In another embodiment the circular sample port is approximately 8 millimeters in diameter. In another embodiment the circular sample port is at least 8 millimeters in diameter. In one embodiment the circular sample port is 9 millimeters in diameter. In another embodiment the circular sample port is approximately 9 millimeters in diameter. In another embodiment the circular sample port is at least 9 millimeters in diameter. In one embodiment the circular sample port is 10 millimeters in diameter. In another embodiment the circular sample port is approximately 10 millimeters in diameter. In another embodiment the circular sample port is at least 10 millimeters in diameter. In one embodiment the circular sample port is 11 millimeters in diameter. In another embodiment the circular sample port is approximately 11 millimeters in diameter. In another embodiment the circular sample port is at least 11 millimeters in diameter. In one embodiment the circular sample port is 12 millimeters in diameter. In another embodiment the circular sample port is approximately 12 millimeters in diameter. In another embodiment the circular sample port is at least 12 millimeters in diameter. In one embodiment the circular sample port is 13 millimeters in diameter. In another embodiment the circular sample port is approximately 13 millimeters in diameter. In another embodiment the circular sample port is at least 13 millimeters in diameter. In one embodiment the circular sample port is 14 millimeters in diameter. In another embodiment the circular sample port is approximately 14 millimeters in diameter. In another embodiment the circular sample port is at least 14 millimeters in diameter. In one embodiment the circular sample port is 15 millimeters in diameter. In another embodiment the circular sample port is approximately 15 millimeters in diameter. In another embodiment the circular sample port is at least 15 millimeters in diameter. In one embodiment the circular sample port is 16 millimeters in diameter. In another embodiment the circular sample port is approximately 16 millimeters in diameter. In another embodiment the circular sample port is at least 16 millimeters in diameter. In one embodiment the circular sample port is 17 millimeters in diameter. In another embodiment the circular sample port is approximately 17 millimeters in diameter. In another embodiment the circular sample port is at least 17 millimeters in diameter. In one embodiment the circular sample port is 18 millimeters in diameter. In another embodiment the circular sample port is approximately 18 millimeters in diameter. In another embodiment the circular sample port is at least 18 millimeters in diameter. In one embodiment the circular sample port is 19 millimeters in diameter. In another embodiment the circular sample port is approximately 19 millimeters in diameter. In another embodiment the circular sample port is at least 19 millimeters in diameter. In one embodiment the circular sample port is 20 millimeters in diameter. In another embodiment the circular sample port is approximately 20 millimeters in diameter. In another embodiment the circular sample port is at least 20 millimeters in diameter.

The sample port shapes and sizes described in this paragraph can apply equally to the sample port and the sample port insert. In several embodiments the present invention provides a test strip housing having an oval-shaped sample port. An oval has a large or major diameter and a small or minor diameter. The large diameter is the length of the straight line that passes through the center of the oval between the two farthest points located along its perimeter and can also be thought of as the length of the oval at its longest point. The small diameter is the length of the straight line that passes through the center of the oval between the closest two points located along the perimeter of the oval and can also be thought of as the width of the oval at its widest point. In one embodiment the oval sample port is from 6-to 15 millimeters in its small diameter. In another embodiment the oval sample port is from 6-to 10 millimeters in its small diameter. In another embodiment the oval sample port is from 7-to 20 millimeters in its small diameter. In another embodiment the oval sample port has an opening that is from 7-to 15 millimeters in its small diameter. In another embodiment the oval sample port has an opening that is from 7-to 10 millimeters in its small diameter. In another embodiment the oval sample port is from 8-to 20 millimeters in its small diameter. In another embodiment the oval sample port is from 8-to 15 millimeters in its small diameter. In another embodiment the oval sample port is from 8-to 10 millimeters in its small diameter. In another embodiment the oval sample port is from 9-to 20 millimeters in its small diameter. In another embodiment the oval sample port is from 9-to 15 millimeters in its small diameter. In another embodiment the oval sample port is from 9-to 10 millimeters in its small diameter. In another embodiment the oval sample port is from 10-to 20 millimeters in its small diameter. In another embodiment the oval sample port is from 10-to 15 millimeters in its small diameter. In another embodiment the oval sample port is 6 millimeters in its small diameter. In another embodiment the oval sample port is approximately 6 millimeters in its small diameter. In another embodiment the oval sample port is at least 6 millimeters in its small diameter. In one embodiment the oval sample port is 7 millimeters in its small diameter. In another embodiment the oval sample port is approximately 7 millimeters in its small diameter. In another embodiment the oval sample port is at least 7 millimeters in its small diameter. In one embodiment the oval sample port is 8 millimeters in its small diameter. In another embodiment the oval sample port is approximately 8 millimeters in its small diameter. In another embodiment the oval sample port is at least 8 millimeters in its small diameter. In one embodiment the oval sample port is 9 millimeters in its small diameter. In another embodiment the oval sample port is approximately 9 millimeters in its small diameter. In another embodiment the oval sample port is at least 9 millimeters in its small diameter. In one embodiment the oval sample port is 10 millimeters in its small diameter. In another embodiment the oval sample port is approximately 10 millimeters in its small diameter. In another embodiment the oval sample port is at least 10 millimeters in its small diameter. In one embodiment the oval sample port is 11 millimeters in its small diameter. In another embodiment the oval sample port is approximately 11 millimeters in its small diameter. In another embodiment the oval sample port is at least 11 millimeters in its small diameter. In one embodiment the oval sample port is 12 millimeters in its small diameter. In another embodiment the oval sample port is approximately 12 millimeters in its small diameter. In another embodiment the oval sample port is at least 12 millimeters in its small diameter. In one embodiment the oval sample port is 13 millimeters in its small diameter. In another embodiment the oval sample port is approximately 13 millimeters in its small diameter. In another embodiment the oval sample port is at least 13 millimeters in its small diameter. In one embodiment the oval sample port is 14 millimeters in its small diameter. In another embodiment the oval sample port is approximately 14 millimeters in its small diameter. In another embodiment the oval sample port is at least 14 millimeters in its small diameter. In one embodiment the oval sample port is 15 millimeters in its small diameter. In another embodiment the oval sample port is approximately 15 millimeters in its small diameter. In another embodiment the oval sample port is at least 15 millimeters in its small diameter. In one embodiment the oval sample port is 16 millimeters in its small diameter. In another embodiment the oval sample port is approximately 16 millimeters in its small diameter. In another embodiment the oval sample port is at least 16 millimeters in its small diameter. In one embodiment the oval sample port is 17 millimeters in its small diameter. In another embodiment the oval sample port is approximately 17 millimeters in its small diameter. In another embodiment the oval sample port is at least 17 millimeters in its small diameter. In one embodiment the oval sample port is 18 millimeters in its small diameter. In another embodiment the oval sample port is approximately 18 millimeters in its small diameter. In another embodiment the oval sample port is at least 18 millimeters in its small diameter. In one embodiment the oval sample port is 19 millimeters in its small diameter. In another embodiment the oval sample port is approximately 19 millimeters in its small diameter. In another embodiment the oval sample port is at least 19 millimeters in its small diameter. In one embodiment the oval sample port is 20 millimeters in its small diameter. In another embodiment the oval sample port is approximately 20 millimeters in its small diameter. In another embodiment the oval sample port is at least 20 millimeters in its small diameter.

The sample port shapes and sizes described in this paragraph can apply equally to the sample port and the sample port insert. In several embodiments the present invention provides a test strip housing having a square shaped sample port of 6-20 millimeters in width/length. In one embodiment the square sample port is from 6-to 15 millimeters in width. In another embodiment the square sample port is from 6-to 10 millimeters in width. In another embodiment the square sample port is from 7-to 20 millimeters in width. In another embodiment the square sample port has an opening that is from 7-to 15 millimeters in width. In another embodiment the square sample port has an opening that is from 7-to 10 millimeters in width. In another embodiment the square sample port is from 8-to 20 millimeters in width. In another embodiment the square sample port is from 8-to 15 millimeters in width. In another embodiment the square sample port is from 8-to 10 millimeters in width. In another embodiment the square sample port is from 9-to 20 millimeters in width. In another embodiment the square sample port is from 9-to 15 millimeters in width. In another embodiment the square sample port is from 9-to 10 millimeters in width. In another embodiment the square sample port is from 10-to 20 millimeters in width. In another embodiment the square sample port is from 10-to 15 millimeters in width. In another embodiment the square sample port is 6 millimeters in width. In another embodiment the square sample port is approximately 6 millimeters in width. In another embodiment the square sample port is at least 6 millimeters in width. In one embodiment the square sample port is 7 millimeters in width. In another embodiment the square sample port is approximately 7 millimeters in width. In another embodiment the square sample port is at least 7 millimeters in width. In one embodiment the square sample port is 8 millimeters in width. In another embodiment the square sample port is approximately 8 millimeters in width. In another embodiment the square sample port is at least 8 millimeters in width. In one embodiment the square sample port is 9 millimeters in width. In another embodiment the square sample port is approximately 9 millimeters in width. In another embodiment the square sample port is at least 9 millimeters in width. In one embodiment the square sample port is 10 millimeters in width. In another embodiment the square sample port is approximately 10 millimeters in width. In another embodiment the square sample port is at least 10 millimeters in width. In one embodiment the square sample port is 11 millimeters in width. In another embodiment the square sample port is approximately 11 millimeters in width. In another embodiment the square sample port is at least 11 millimeters in width. In one embodiment the square sample port is 12 millimeters in width. In another embodiment the square sample port is approximately 12 millimeters in width. In another embodiment the square sample port is at least 12 millimeters in width. In one embodiment the square sample port is 13 millimeters in width. In another embodiment the square sample port is approximately 13 millimeters in width. In another embodiment the square sample port is at least 13 millimeters in width. In one embodiment the square sample port is 14 millimeters in width. In another embodiment the square sample port is approximately 14 millimeters in width. In another embodiment the square sample port is at least 14 millimeters in width. In one embodiment the square sample port is 15 millimeters in width. In another embodiment the square sample port is approximately 15 millimeters in width. In another embodiment the square sample port is at least 15 millimeters in width. In one embodiment the square sample port is 16 millimeters in width. In another embodiment the square sample port is approximately 16 millimeters in width. In another embodiment the square sample port is at least 16 millimeters in width. In one embodiment the square sample port is 17 millimeters in width. In another embodiment the square sample port is approximately 17 millimeters in width. In another embodiment the square sample port is at least 17 millimeters in width. In one embodiment the square sample port is 18 millimeters in width. In another embodiment the square sample port is approximately 18 millimeters in width. In another embodiment the square sample port is at least 18 millimeters in width. In one embodiment the square sample port is 19 millimeters in width. In another embodiment the square sample port is approximately 19 millimeters in width. In another embodiment the square sample port is at least 19 millimeters in width. In one embodiment the square sample port is 20 millimeters in width. In another embodiment the square sample port is approximately 20 millimeters in width. In another embodiment the square sample port is at least 20 millimeters in width.

The sample port shapes and sizes described in this paragraph can apply equally to the sample port and the sample port insert. In several embodiments the present invention provides a test strip housing having a rectangular shaped sample port of 6-20 millimeters in width. The term "width," as used in relation to a rectangular shaped sample port herein, refers to the dimension of the shortest sides of the rectangle. In one embodiment the rectangular sample port is from 6-to 15 millimeters in width. In another embodiment the rectangular sample port is from 6-to 10 millimeters in width. In another embodiment the rectangular sample port is from 7-to 20 millimeters in width. In another embodiment the rectangular sample port has an opening that is from 7-to 15 millimeters in width. In another embodiment the rectangular sample port has an opening that is from 7-to 10 millimeters in width. In another embodiment the rectangular sample port is from 8-to 20 millimeters in width. In another embodiment the rectangular sample port is from 8-to 15 millimeters in width. In another embodiment the rectangular sample port is from 8-to 10 millimeters in width. In another embodiment the rectangular sample port is from 9-to 20 millimeters in width. In another embodiment the rectangular sample port is from 9-to 15 millimeters in width. In another embodiment the rectangular sample port is from 9-to 10 millimeters in width. In another embodiment the rectangular sample port is from 10-to 20 millimeters in width. In another embodiment the rectangular sample port is from 10-to 15 millimeters in width. In another embodiment the rectangular sample port is 6 millimeters in width. In another embodiment the rectangular sample port is approximately 6 millimeters in width. In another embodiment the rectangular sample port is at least 6 millimeters in width. In one embodiment the rectangular sample port is 7 millimeters in width. In another embodiment the rectangular sample port is approximately 7 millimeters in width. In another embodiment the rectangular sample port is at least 7 millimeters in width. In one embodiment the rectangular sample port is 8 millimeters in width. In another embodiment the rectangular sample port is approximately 8 millimeters in width. In another embodiment the rectangular sample port is at least 8 millimeters in width. In one embodiment the rectangular sample port is 9 millimeters in width. In another embodiment the rectangular sample port is approximately 9 millimeters in width. In another embodiment the rectangular sample port is at least 9 millimeters in width. In one embodiment the rectangular sample port is 10 millimeters in width. In another embodiment the rectangular sample port is approximately 10 millimeters in width. In another embodiment the rectangular sample port is at least 10 millimeters in width. In one embodiment the rectangular sample port is 11 millimeters in width. In another embodiment the rectangular sample port is approximately 11 millimeters in width. In another embodiment the rectangular sample port is at least 11 millimeters in width. In one embodiment the rectangular sample port is 12 millimeters in width. In another embodiment the rectangular sample port is approximately 12 millimeters in width. In another embodiment the rectangular sample port is at least 12 millimeters in width. In one embodiment the rectangular sample port is 13 millimeters in width. In another embodiment the rectangular sample port is approximately 13 millimeters in width. In another embodiment the rectangular sample port is at least 13 millimeters in width. In one embodiment the rectangular sample port is 14 millimeters in width. In another embodiment the rectangular sample port is approximately 14 millimeters in width. In another embodiment the rectangular sample port is at least 14 millimeters in width. In one embodiment the rectangular sample port is 15 millimeters in width. In another embodiment the rectangular sample port is approximately 15 millimeters in width. In another embodiment the rectangular sample port is at least 15 millimeters in width. In one embodiment the rectangular sample port is 16 millimeters in width. In another embodiment the rectangular sample port is approximately 16 millimeters in width. In another embodiment the rectangular sample port is at least 16 millimeters in width. In one embodiment the rectangular sample port is 17 millimeters in width. In another embodiment the rectangular sample port is approximately 17 millimeters in width. In another embodiment the rectangular sample port is at least 17 millimeters in width. In one embodiment the rectangular sample port is 18 millimeters in width. In another embodiment the rectangular sample port is approximately 18 millimeters in width. In another embodiment the rectangular sample port is at least 18 millimeters in width. In one embodiment the rectangular sample port is 19 millimeters in width. In another embodiment the rectangular sample port is approximately 19 millimeters in width. In another embodiment the rectangular sample port is at least 19 millimeters in width. In one embodiment the rectangular sample port is 20 millimeters in width. In another embodiment the rectangular sample port is approximately 20 millimeters in width. In another embodiment the rectangular sample port is at least 20 millimeters in width.

The sample port shapes and sizes described in this paragraph can apply equally to the sample port and the sample port insert. In several embodiments the present invention provides a test strip housing having sample port with a convex polygonal shape of 6-20 millimeters in width. The term "width," as used in relation to a convex polygonal shaped sample port herein, refers to the dimension of the shortest straight line that passes from one side of the polygon to the other through the polygons central point. In one embodiment the polygonal sample port is from 6-to 15 millimeters in width. In another embodiment the polygonal sample port is from 6-to 10 millimeters in width. In another embodiment the polygonal sample port is from 7-to 20 millimeters in width. In another embodiment the polygonal sample port has an opening that is from 7-to 15 millimeters in width. In another embodiment the polygonal sample port has an opening that is from 7-to 10 millimeters in width. In another embodiment the polygonal sample port is from 8-to 20 millimeters in width. In another embodiment the polygonal sample port is from 8-to 15 millimeters in width. In another embodiment the polygonal sample port is from 8-to 10 millimeters in width. In another embodiment the polygonal sample port is from 9-to 20 millimeters in width. In another embodiment the polygonal sample port is from 9-to 15 millimeters in width. In another embodiment the polygonal sample port is from 9-to 10 millimeters in width. In another embodiment the polygonal sample port is from 10-to 20 millimeters in width. In another embodiment the polygonal sample port is from 10-to 15 millimeters in width. In another embodiment the polygonal sample port is 6 millimeters in width. In another embodiment the polygonal sample port is approximately 6 millimeters in width. In another embodiment the polygonal sample port is at least 6 millimeters in width. In one embodiment the polygonal sample port is 7 millimeters in width. In another embodiment the polygonal sample port is approximately 7 millimeters in width. In another embodiment the polygonal sample port is at least 7 millimeters in width. In one embodiment the polygonal sample port is 8 millimeters in width. In another embodiment the polygonal sample port is approximately 8 millimeters in width. In another embodiment the polygonal sample port is at least 8 millimeters in width. In one embodiment the polygonal sample port is 9 millimeters in width. In another embodiment the polygonal sample port is approximately 9 millimeters in width. In another embodiment the polygonal sample port is at least 9 millimeters in width. In one embodiment the polygonal sample port is 10 millimeters in width. In another embodiment the polygonal sample port is approximately 10 millimeters in width. In another embodiment the polygonal sample port is at least 10 millimeters in width. In one embodiment the polygonal sample port is 11 millimeters in width. In another embodiment the polygonal sample port is approximately 11 millimeters in width. In another embodiment the polygonal sample port is at least 11 millimeters in width. In one embodiment the polygonal sample port is 12 millimeters in width. In another embodiment the polygonal sample port is approximately 12 millimeters in width. In another embodiment the polygonal sample port is at least 12 millimeters in width. In one embodiment the polygonal sample port is 13 millimeters in width. In another embodiment the polygonal sample port is approximately 13 millimeters in width. In another embodiment the polygonal sample port is at least 13 millimeters in width. In one embodiment the polygonal sample port is 14 millimeters in width. In another embodiment the polygonal sample port is approximately 14 millimeters in width. In another embodiment the polygonal sample port is at least 14 millimeters in width. In one embodiment the polygonal sample port is 15 millimeters in width. In another embodiment the polygonal sample port is approximately 15 millimeters in width. In another embodiment the polygonal sample port is at least 15 millimeters in width. In one embodiment the polygonal sample port is 16 millimeters in width. In another embodiment the polygonal sample port is approximately 16 millimeters in width. In another embodiment the polygonal sample port is at least 16 millimeters in width. In one embodiment the polygonal sample port is 17 millimeters in width. In another embodiment the polygonal sample port is approximately 17 millimeters in width. In another embodiment the polygonal sample port is at least 17 millimeters in width. In one embodiment the polygonal sample port is 18 millimeters in width. In another embodiment the polygonal sample port is approximately 18 millimeters in width. In another embodiment the polygonal sample port is at least 18 millimeters in width. In one embodiment the polygonal sample port is 19 millimeters in width. In another embodiment the polygonal sample port is approximately 19 millimeters in width. In another embodiment the polygonal sample port is at least 19 millimeters in width. In one embodiment the polygonal sample port is 20 millimeters in width. In another embodiment the polygonal sample port is approximately 20 millimeters in width. In another embodiment the polygonal sample port is at least 20 millimeters in width.

Result Viewing Port

As used herein the term "result viewing port" refers to an area in a test strip housing through which the result area of a test strip located within a housing can be seen. Typically at least a portion of both a test and control result area on a test strip will be visible through a result viewing port.

In one embodiment, the present invention provides a test strip housing having one or more result viewing ports that are of a sufficient size and shape to allow visualization of at least a portion of the result area of a test strip. In the Figures provided here exemplary test strip housings having a single result viewing port are shown. However, test strip housings according to the invention may have one, two, three, four, or more result viewing ports, as desired. The result viewing port can be of any suitable size and shape. Suitable shapes for the result viewing port include, but are not limited to, circular, oval, square, rectangular, polygonal and the like.

In some embodiments the result viewing port may constitute an actual opening in the housing through which an underlying test strip could, in theory, be touched (e.g. by hand or with a tool). In other embodiments the result viewing port may comprise an area of the housing through which the result area of an underlying test strip could be viewed but that would not allow an underlying test strip to be touched. In such embodiments the result viewing port may constitute or comprise a transparent material. In other embodiments the result viewing port may constitute an actual opening in the housing with a transparent material/window placed into or over the opening.

In embodiments where the result viewing port comprises an actual opening in the housing, the opening will typically have a top edge(s) on the top surface of the housing (see, for example, element 2a in the Figures), a bottom edge(s) below the top surface of the housing and above the test strip itself (see, for example, element 2b in the Figures), and sidewalls (see, for example, element 2c in the Figures). The top and bottom of the result viewing port opening may be comprise straight, curved edges, or a combination of straight and curved edges, and may form an opening of any suitable shape. For example, in one embodiment the opening may be circular or oval shaped. In another embodiment the opening may have any suitable polygonal shape, including, but not limited to, a triangular, square, rectangular, pentagonal, or hexagonal shape. The side walls of the opening that constitutes the result viewing port may run perpendicular to the top surface of the test strip housing or not, and may be straight, curved, beveled, chamfered, or any other suitable shape, as desired. The top and bottom edges of the result viewing port opening may have the same size and/or shape as each other or may have different sizes and/or shapes. The result viewing ports shown in the Figures, which are exemplary only, have top and bottom edges that are both of the same size and that are rectangular shape (FIG. 5 to 8) or oval shape (FIGS. 1 to 3). However, result viewing ports can have top and bottom edges that differ in size or shape as desired. For example, in some embodiments, the result viewing port may have a bottom edge that has smaller dimensions than the top edge resulting in a tapered opening. The sides of such a tapered opening could be of any suitable form, including, but not limited to, being curved, straight, beveled, or chamfered. In other embodiments, the result viewing port may have a bottom edge that has different geometric shape as compared to the top edge, for example being square or rectangular at the top edge and circular or oval shaped at the bottom edge. The result viewing port can be of any size that is sufficient to allow visualization of at least a portion of the result area of a test strip located inside the housing.

Test Strip Cover

In one embodiment the present invention provides a test strip housing system in which a cover can be placed over at least the sample port(s), and ideally also the result-viewing port(s), of the test strip housing after the test sample has been applied to the test strip—in order to minimize the risk to test administrators and others that they might come into contact with potentially hazardous and/or infectious material on the test strip or the test strip housing.

FIGS. 5 to 8 show some exemplary embodiments in which the cover has a rectangular box-like shape with openings at each end, such that the cover can be slid over a rectangular shaped but slightly smaller test strip housing—similar to the way in which a match box lid can be slid over a match box. However, the cover can be of any suitable shape and size sufficient to allow it to be slid over the test strip housing with which it is to be used. For example, FIGS. 1 to 4 illustrate embodiments in which the cover covers only the top surface 1a of the test strip housing. Typically the cover will have an internal geometric shape that is similar to the exterior geometric shape of the test strip housing with which it will be used but will have: (a) internal cross-sectional dimensions (such as width, depth, diameter, cross-sectional area, and the like) that are slightly larger than the corresponding external cross-sectional dimensions of the test strip housing with which it will be used, and (b) have at least one open end such that the cover can be slid over the test strip housing with which it will be used.

In some embodiments the cover may be shorter in length than the test strip housing with which it will be used and open at each end—as shown in FIGS. 5-8. In such embodiments the cover can be any length sufficient that, when slid into position 2, the sample port(s) on the test strip housing are covered by the cover. However, in preferred embodiments, as shown in FIGS. 1-8, the cover should be of a length sufficient that, when slid into position 2, the cover covers both the sample port(s) and the result viewing window(s) on the test strip housing.

In some embodiments the cover may be of the same length, or longer than, the test strip housing. In such embodiments the cover need not be open at each end. Instead the cover need only be open at the end that will slide over the sample port on the test strip housing, while the other end (closest to the result viewing window) can be closed. In such embodiments the cover will, when slid into position 2, necessarily cover both the sample port(s) and the result viewing window(s) on the test strip housing.

In some embodiments the cover may cover only the top surface, or a portion thereof, of the test strip housing. In such embodiments the cover may comprise a tongue and groove design to align the cover on the test strip housing and facilitate sliding of the cover over the top surface of the test strip housing. For example, the long edges of the test strip housing can comprise grooves or indentations into which fits a tongue or other suitable protrusion on the cover. As another example, the cover can comprise grooves or indentations into which fits a tongue or other suitable protrusion on the long edges of the test strip housing.

FIGS. 1 and 6 show a cover 4 positioned over a test strip housing 1 in a first position in which the sample port is not covered. A test sample may be applied to the sample port 2 while the cover 4 is in this first position. After a test sample has been applied to the sample port the cover 4 may be slid over the test strip housing 1 and into a second position in which the sample port is covered, and depending on the length of the cover, the result viewing window may also be covered, as shown in FIGS. 2 and 7.

The cover may be made of any suitable material. In one embodiment the cover is made of plastic, such as a biocompatible plastic. The cover may be transparent, translucent, or opaque. In some embodiments the cover is made of a transparent material or comprises a transparent window such that the result viewing port is visible even with the cover in position two (the second position) on the test strip housing. This allows test administrators, health care providers, patients and others to continue to view the result viewing port, and even photograph or photocopy the result, even after the cover has been placed into its second position.

Locking System

It is one object of the invention to provide a system in which a cover can be placed over a used test strip housing in order to minimize the risk to test administrators and others that might otherwise come into contact with potentially hazardous and/or infectious material on the test strip or the test strip housing. In some such embodiments it can be advantageous to use a locking system to lock the cover to the test strip housing in position 2. For example, in one embodiment a test sample may be applied to the sample port 2 while the cover 4 is in this first position, and then, after a test sample has been applied to the sample port, the cover 4 may be slid over the test strip housing and locked into a second position in which the sample port, and optionally also the result viewing port, is covered. Locking the cover to the test strip housing in position 2 prevents the cover sliding back to expose the sample port, or the result viewing window, and thus further minimizes the risk to test administrators and others.

FIG. 8 shows one exemplary locking system that comprises a protrusion 5 (here, a hook) located towards the proximal end of the cover 4, and a receptacle 6 located towards the proximal end of the test strip housing 1. When the cover 4 is slid from its first position (FIG. 8A) to its second position (FIG. 8B) the protrusion 5 engages with the receptacle 6 and locks the cover to the test strip housing. FIGS. 1 and 3 show another exemplary locking system that comprises a protrusion 5 located on the test strip housing 1 and a receptacle 6 located on the cover. When the cover 4 is slid from its first position to its second position the protrusion 5 engages with the receptacle 6 and locks the cover to the test strip housing. The locking systems shown in FIGS. 1 and 8 are not the only type of locking systems that can be used. Rather, any suitable type of locking system may be used. In one embodiment, the locking system comprises one or more protrusions located towards the proximal end of the cover and one or more receptacles located towards the proximal end of the test strip housing, wherein in use the protrusion will engage with the receptacle while the cover is in position 2 on the test strip housing, thereby locking the cover to the test strip housing. In another embodiment, the locking system comprises one or more protrusions located towards the proximal end of the test strip housing and one or more receptacles located towards the proximal end of the cover, wherein, in use, one or more of the protrusions will engage with one or more of the receptacles when the cover is slid to position 2 on the test strip housing, thereby locking the cover to the test strip housing. Suitable forms for the protrusions include, but are not limited to, hooks, claws, nodules, pins, plugs, clips, latches and any other suitable structure that protrudes from the surface of either the cover or the test strip housing. The receptacle can be any indentation or hole within the surface of either the cover or the test strip housing that can receive the protrusion. In some embodiments the protrusions and the receptacles have complementary shapes. In some embodiments the protrusion can be spring mounted so that it is only released when in position over its receptacle. In some embodiments the protrusion and the receptacle are magnetic. In some embodiments the protrusion and the receptacle engage one another in a reversible manner, such that the cover is locked to the housing reversibly. In such embodiments it is preferred that considerable force is needed to disengage the protrusion from the receptacle in order to reduce the chance that the cover could accidentally become unlocked. In other embodiments the protrusion and the receptacle engage one another in an irreversible manner, such that the cover is locked to the housing irreversibly.

Applications

The safety features described herein can be used in conjunction with any diagnostic test strip system. For example, it can be used with test strip systems used to test water samples (e.g. for water-borne agents), food samples (e.g. for food-borne agents), blood samples, serum samples, urine samples, stool samples, saliva samples, or samples or any other biological fluid or liquid substance to be tested. Examples of the types of diagnostic tests that can be used in conjunction with the improved test strip housing systems of the present invention include, but are not limited to, pregnancy tests, fertility tests, HIV tests, malaria tests, flu tests, drug tests (e.g. for detection of drugs of abuse), and the like—without limitation.

The invention may also be further defined in terms of the following claims.

The invention claimed is:

1. A diagnostic test strip system comprising:
    (a) a test strip housing comprising:
        (i) a sample port of sufficient size to allow placement of a human patient's finger or thumb therein, wherein the sample port is selected from the group consisting of: a circular-shaped sample port with a diameter of at least 15 mm, an oval-shaped sample port with a small diameter of at least 15 mm, a square-shaped sample port with sides of at least 15 mm in length, a rectangular-shaped sample port with a width of at least at least 15 mm, and a polygonal-shaped sample port with a width of at least 15 mm, and
        (ii) a result viewing port,
    (b) a unitary cover slidable between a first position and a second position on the test strip housing and having a length such that in the first position the cover does not cover the sample port and in the second position the cover completely covers both the sample port and the result viewing port, and
    (c) a locking system that locks the cover to the test strip housing in the second position on the test strip housing.

2. The diagnostic test strip system of claim 1, wherein the cover is transparent.

3. The diagnostic test strip system of claim 2, wherein the result viewing port is visible through the cover in the second position.

4. The diagnostic test strip system of claim 1, wherein the cover comprises a transparent window, and wherein the result viewing port is visible through the transparent window of the cover in the second position.

5. The diagnostic test strip system of claim 1, wherein the locking system comprises a protrusion on the cover and a receptacle on the test strip housing, positioned such that the protrusion is engageable with the receptacle when the cover is in the second position.

6. The diagnostic test strip system of claim 5, wherein the protrusion is a hook and the receptacle is a hole or indentation.

7. The diagnostic test strip system of claim 1, wherein the locking system comprises a protrusion on the test strip housing and a receptacle on the cover, positioned such that the protrusion is engageable with the receptacle wherein the cover is in the second position.

8. The diagnostic test strip system of claim 7, wherein the protrusion is a hook and the receptacle is a hole or indentation.

9. The diagnostic test strip system of claim 1, further comprising a test strip within the test strip housing, the test strip comprising a sample pad aligned with sample port of the test strip housing, and a result area aligned with the result viewing port of the test strip housing.

10. The diagnostic test strip system of claim 1, wherein the test strip housing further comprises internal grooves, indentations, holes, walls, bars or pins adapted to hold and position a test strip within the test strip housing.

11. The diagnostic test strip system of claim 1, wherein the sample port is a circular-shaped sample port with a diameter of at least 20 mm, an oval-shaped sample port with a small diameter of at least 20 mm, a square-shaped sample port with sides of at least 20 mm in length, a rectangular-shaped sample port with a width of at least at least 20 mm, or a polygonal-shaped sample port with a width of at least 20 mm.

12. A diagnostic test strip system comprising:
   (a) a test strip comprising a sample pad and a result area,
   (b) a test strip housing that contains the test strip and that comprises:
      (i) a sample port aligned with the sample pad of the test strip that is of sufficient size to allow placement of a human patient's finger or thumb therein, wherein the sample port is selected from the group consisting of: a circular-shaped sample port with a diameter of at least 15 mm, an oval-shaped sample port with a small diameter of at least 15 mm, a square-shaped sample port with sides of at least 15 mm in length, a rectangular-shaped sample port with a width of at least at least 15 mm, and a polygonal-shaped sample port with a width of at least 15 mm, and
      (ii) a result viewing port aligned with the result area of the test strip,
   (c) a unitary cover slidable between a first position and a second position on the test strip housing and having a length such that in the first position the cover does not cover the sample port and in the second position the cover completely covers both the sample port and the result viewing port, and
   (d) a locking system that locks the cover to the test strip housing in the second position on the test strip housing.

13. The diagnostic test strip system of claim 12, wherein the cover is transparent.

14. The diagnostic test strip system of claim 12, wherein the result viewing port is visible through the cover in the second position.

15. The diagnostic test strip system of claim 12, wherein the cover comprises a transparent window, and wherein the result viewing port is visible through the transparent window of the cover in the second position.

16. The diagnostic test strip system of claim 12, wherein the, locking system comprises either: (i) a receptacle on the test strip housing and a protrusion on the cover that is engageable with the receptacle when the cover is in the second position, or (ii) a receptacle on the cover and a protrusion on the test strip housing that is engageable with the receptacle when the cover is in the second position.

17. The diagnostic test strip system of claim 12 wherein the test strip housing further comprises internal grooves, indentations, holes, walls, bars or pins adapted to hold and position the test strip within the test strip housing.

18. The diagnostic test strip system of claim 12, wherein the sample port is a circular-shaped sample port with a diameter of at least 20 mm, an oval-shaped sample port with a small diameter of at least 20 mm, a square-shaped sample port with sides of at least 20 mm in length, a rectangular-shaped sample port with a width of at least at least 20 mm, or a polygonal-shaped sample port with a width of at least 20 mm.

19. A diagnostic test strip system comprising:
   (a) a test strip comprising a sample pad and a result area,
   (b) a test strip housing that contains the test strip and that comprises:
      (i) a sample port aligned with the sample pad of the test strip that is of sufficient size to allow placement of a human patient's finger or thumb therein, wherein the sample port is selected from the group consisting of: a circular-shaped sample port with a diameter of at least 15 mm, an oval-shaped sample port with a small diameter of at least 15 mm, a square-shaped sample port with sides of at least 15 mm in length, a rectangular-shaped sample port with a width of at least at least 15 mm, and a polygonal-shaped sample port with a width of at least 15 mm, and
      (ii) a result viewing port aligned with the result area of the test strip,
   (c) a unitary cover slidable between a first position and a second position on the test strip housing and having a length such that in the first position the cover does not cover the sample port and in the second position the cover completely covers both the sample port and the result viewing port, and
   (d) a locking system that locks the cover to the test strip housing in the second position completely covering both the sample port and the result viewing port on the test strip housing, wherein the locking system comprises either: (i) a receptacle on the test strip housing and a protrusion on the cover that is engageable with the receptacle when the cover is in the second position, or (ii) a receptacle on the cover and a protrusion on the test strip housing that is engageable with the receptacle when the cover is in the second position.

20. The diagnostic test strip system of claim 19, wherein the sample port is a circular-shaped sample port with a diameter of at least 20 mm, an oval-shaped sample port with a small diameter of at least 20 mm, a square-shaped sample port with sides of at least 20 mm in length, a rectangular-shaped sample port with a width of at least at least 20 mm, or a polygonal-shaped sample port with a width of at least 20 mm.

* * * * *